United States Patent
Elmaleh

(10) Patent No.: US 9,675,284 B2
(45) Date of Patent: Jun. 13, 2017

(54) APPARATUS AND METHOD FOR DETECTING AND\OR MONITORING ONE OR MORE COMPOUNDS IN BLOOD

(71) Applicant: David R. Elmaleh, Newton, MA (US)

(72) Inventor: David R. Elmaleh, Newton, MA (US)

(73) Assignee: David R. Elmaleh, Newton, MA (US)

( * ) Notice: Subject to any disclaimer, the term of this patent is extended or adjusted under 35 U.S.C. 154(b) by 156 days.

(21) Appl. No.: 14/070,081

(22) Filed: Nov. 1, 2013

(65) Prior Publication Data

US 2014/0243636 A1 Aug. 28, 2014

Related U.S. Application Data

(60) Provisional application No. 61/721,258, filed on Nov. 1, 2012.

(51) Int. Cl.
*B01L 3/02* (2006.01)
*A61B 5/145* (2006.01)
*A61B 5/15* (2006.01)
*A61B 5/157* (2006.01)

(52) U.S. Cl.
CPC ........ *A61B 5/14532* (2013.01); *A61B 5/1411* (2013.01); *A61B 5/157* (2013.01); *A61B 5/150022* (2013.01); *A61B 5/150396* (2013.01); *A61B 5/150419* (2013.01); *A61B 5/150969* (2013.01); *A61B 5/150984* (2013.01)

(58) Field of Classification Search
CPC .. A61M 37/0015; A61M 37/003; A61M 5/00; A61M 5/46
USPC ............................................ 422/509; 269/38
See application file for complete search history.

(56) References Cited

U.S. PATENT DOCUMENTS

| | | | |
|---|---|---|---|
| 7,344,499 B1 | 3/2008 | Prausnitz et al. | |
| 8,303,518 B2 | 11/2012 | Aceti et al. | |
| 2002/0132054 A1* | 9/2002 | Trautman et al. | 427/372.2 |
| 2007/0060867 A1 | 3/2007 | Xu | |
| 2008/0125743 A1* | 5/2008 | Yuzhakov | A61M 37/0015 604/506 |
| 2009/0143749 A1 | 6/2009 | Sugimura et al. | |
| 2011/0105952 A1* | 5/2011 | Bernstein et al. | 600/573 |
| 2011/0306853 A1* | 12/2011 | Black et al. | 600/309 |
| 2012/0041337 A1* | 2/2012 | Ferguson et al. | 600/573 |
| 2012/0080119 A1 | 4/2012 | Makino et al. | |
| 2012/0259311 A1* | 10/2012 | Hirshberg | 604/506 |

OTHER PUBLICATIONS

Sioss et al., "Silica-Coated, Au/Ag Striped Nanowires for Bioanalysis", Langmuir, 23 (22), pp. 11334-11341 (2007) (Abstract Only).
Dean et al., "Organically Modified Silicas on Metal Nanowires", Langmuir, 26(18), pp. 14861-14870, Sep. 21, 2010.
Yadav et al., "Microneedles: Promising Technique for Transdermal Drug Delivery." International Journal of Pharma and Bio Sciences, vol. 2, Issue 1, pp. 684-708, Jan.-Mar. 2011.
Office Action for U.S. Appl. No. 14/963,195, mailed Sep. 23, 2016.
International Search Report of PCT Application No. PCT/US2016/065670, mailed Feb. 17, 2017.

* cited by examiner

*Primary Examiner* — Jill Warden
*Assistant Examiner* — Brittany Fisher
(74) *Attorney, Agent, or Firm* — Pearl Cohen Zedek Latzer Baratz LLP

(57) ABSTRACT

A platform has microneedles for determining blood levels of compound of interest, such as glucose.

17 Claims, 5 Drawing Sheets

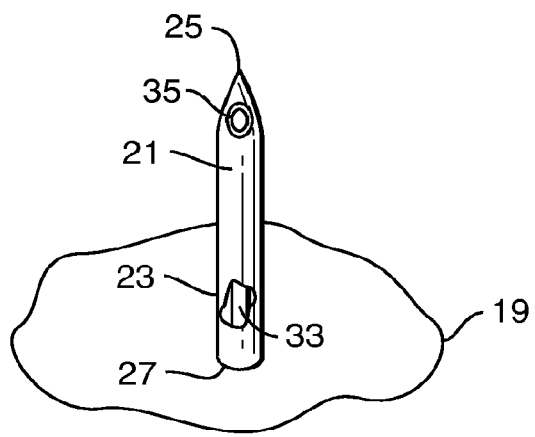
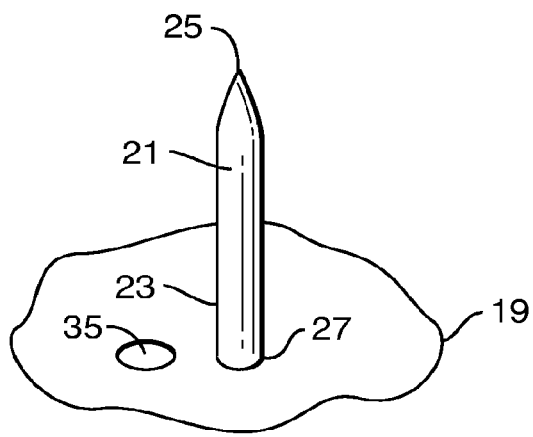
FIG. 3A  FIG. 3B
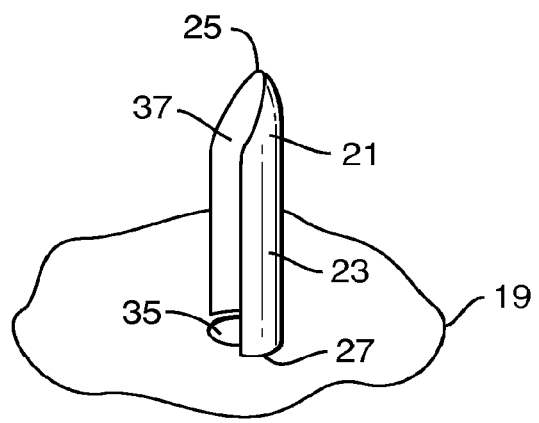
FIG. 3C

APPARATUS AND METHOD FOR DETECTING AND\OR MONITORING ONE OR MORE COMPOUNDS IN BLOOD

CROSS REFERENCE TO RELATED APPLICATION

This application claims the benefit of U.S. Provisional Patent Application No. 61/721,258, filed Nov. 1, 2012.

FIELD OF THE INVENTION

Embodiments of the present invention are directed to devices and methods for sampling blood, with particular application for the detection and monitoring of glucose for diabetic conditions.

BACKGROUND OF THE INVENTION

Several conditions require sampling of blood. The sampling of blood can be used to determine the blood level of drugs with narrow therapeutic ranges, determine compliance or detect drugs of abuse. Blood sampling may also be necessary to determine adequate control of a disease state where, for example, without limitation, the patient can not regulate the level of a compound. For example, diabetics do not have the ability to control glucose levels in the blood to maintain such levels in a normal range. Glucose blood levels are needed to regulate the administration of insulin or other hypoglycemic or hyperglycemic agent.

Diabetics need to test blood levels several times a day. However, the experience is not pleasant. There is pain associated with sticking a lance into the flesh in order to draw blood. Prolonged and repeated sticking causes skin abrasion as well. There is a psychological aversion to sticking a lance into oneself. Patient compliance for testing blood glucose levels is a problem.

It would be desirable to be able to test blood levels of biologically important compounds, such as glucose, or drugs without discomfort or the aversion of sticking a lance.

SUMMARY OF THE INVENTION

Embodiments of the present invention feature devices and methods for sampling blood without pain and without initiating the psychological aversion of sticking oneself with a lance. One embodiment, directed to a device for sampling blood, comprises a platform having a planar configuration having a top surface and a bottom surface. The bottom surface has one or more microneedles projecting therefrom and each microneedle has an elongated body having a first end and a second end. The first end is formed as a tip and the second end is formed as a base affixed to the bottom surface of the platform. The elongated body has a diameter of about 50 to 500 microns and a length of about 200 to 1500 microns. The platform has a passage opening in the top surface and a passage extending therefrom to a withdrawal opening in at least one of the bottom surface, the elongated body and at or about the tip. The withdrawal opening in the bottom surface in an area is closely associated with one or more microneedle bases for cooperating with one or more microneedles to receive a fluid sample withdrawn from the skin surface as the one or more microneedles are placed on and pressed into the skin of a user. The withdrawal opening in the elongated member or at or about the tip is for receiving one or more fluid samples withdrawn as the one or more microneedles are placed on and pressed into the skin of a user. The microneedles, having a small size in diameter and in length, do not reach nerve ending and do not elicit a pain response.

In the location in the elongated member or tip, the withdrawal opening is closer to blood vessels. The position of the withdrawal opening can be a mixture of locations and comprise all locations. For example, without limitation the microneedles may have a cross sectional "U" shape and define a withdrawal opening from the bottom surface to along the elongated member to the tip.

Embodiments of the present device feature a platform having an array or plurality of microneedles. For example, one array features between 1-50 microneedles, and more preferably 1-10 microneedles.

Embodiments of the present invention are ideally suited for use with a reader. The reader analyses the sample to determine the presence or absence or quantity of one or more compounds of interest. For example, without limitation, for individuals afflicted with diabetes, the compound of interest is glucose. Readers for monitoring glucose levels are well known in the art. Embodiments of the present invention feature a platform of the present device affixed to the reader such that the passage is in fluid communication with the test elements of the reader. The device of the present invention can be permanently affixed or releaseably affixed allowing the devices to be removed after usage and replaced with unused devices. Replaceable devices allow the user to be more certain as to the clean and preferably sterile or near sterile microneedle surfaces.

Some readers feature capillary channeling strips for receiving a blood sample. Such channeling strips or test strips can be integrally affixed to the platform or be removably received on the platform. Embodiments of the present invention feature devices for use with such readers. One embodiment features a device further comprising a platform cover forming a conduit in communication with the passage opening for transporting blood or a blood fraction to a reader. A further embodiment comprises a test strip received or integrally affixed to a least one of the platform and platform cover in fluid communication with the conduit for transporting blood or a blood fraction to the reader. Fluid moves through the test strip by capillary action, laminar flow, vacuum, adsorption or other means.

One platform cover of the present invention features window means which allows the user to see that the conduit has a blood sample. As used herein, window means refers to a transparent or semi transparent film, membrane, plastic piece which permits one to visualize the conduit from empty to having sample, by color change or direct visualization of the sample.

Embodiments of the present invention feature a device further comprising packaging for holding said platform in a controlled environment. A controlled environment in the present context refers to clean, sterile or near sterile status. Embodiments of the present invention feature packaging that facilitate use of the device. For example, one embodiment features a plurality of platforms aligned in strips or groups with each platform secured in a separate controlled environment. The groups comprise number of platforms which a user is likely to use during a day, or the strips allow the user to determine a number of platforms desired and allow such number to be separated from a bulk supply of platforms by a tear strip.

Embodiments of the present invention are ideally suited for monitoring blood glucose levels. Diabetics need to check glucose levels regularly and drawing blood is one of the most unpleasant aspects of the disease.

A further embodiment of the present invention is directed to a method of sampling blood. The method comprises the step of providing a platform having a planar configuration, a top surface and a bottom surface. The bottom surface has one or more microneedles projecting therefrom and each microneedle has an elongated body having a first end and a second end. The first end is formed as a tip and the second end is formed as a base. The elongated body has a diameter of about 50-500 microns and a length of 200-1500-microns. The base is affixed to the bottom surface of the platform. The platform has a passage opening in the top surface and a passage extending therefrom to a withdrawal opening in at least one of the bottom surface, the elongated body and at or about the tip. The withdrawal opening in the bottom surface is in an area closely associated with one or more microneedle bases for cooperating with one or more microneedles to receive a fluid sample withdrawn from the skin surface as the one or more microneedles are placed on and pressed into the skin of a user. The withdrawal opening in the elongated member or at or about said tip for receiving one or more fluid samples withdrawn as the one or more microneedles are placed on and pressed into the skin of a user. The method further comprises the step of placing the platform on the skin of a user and pressing the microneedles into the skin to place the withdrawal opening in fluid communication with the user's blood and withdrawing a sample through the passage and out of the passage opening. The microneedles, having a small size in diameter and in length, have minimal or no interaction with nerve ending and do not elicit a pain response.

Embodiments of the present method feature use of a reader to which the platform is attached, integrally affixed to or in fluid communication. For example, the method comprises the step of placing a platform on a reader or placing a platform in fluid communication with a reader and withdrawing a sample which is received and processed by the reader. One embodiment features window means to allow the additional step of checking the platform for the presence of sample.

Again, embodiments of the present invention are ideally suited for glucose monitoring in blood sample of diabetics.

These and other features and advantages will be apparent to those skilled in the art upon viewing the drawings which are briefly described next and reading the detailed description that follows.

BRIEF DESCRIPTION OF THE DRAWINGS

FIG. 3A depicts a microneedle of the present invention;

FIG. 3B depicts a microneedle of the present invention;

FIG. 3C depicts a microneedle of the present invention;

DETAILED DESCRIPTION OF THE INVENTION

Embodiments of the present invention will now be described in detail with respect to devices and methods for sampling blood to monitor glucose levels in blood samples of diabetic individuals. The methods and devices described are considered to be the best mode to make and use embodiments of the present invention. However, such embodiments of the present invention are subject to modification and alteration and the best mode contemplated may change over time. Therefore, the present description should be considered exemplary and not limiting.

Figure 1:
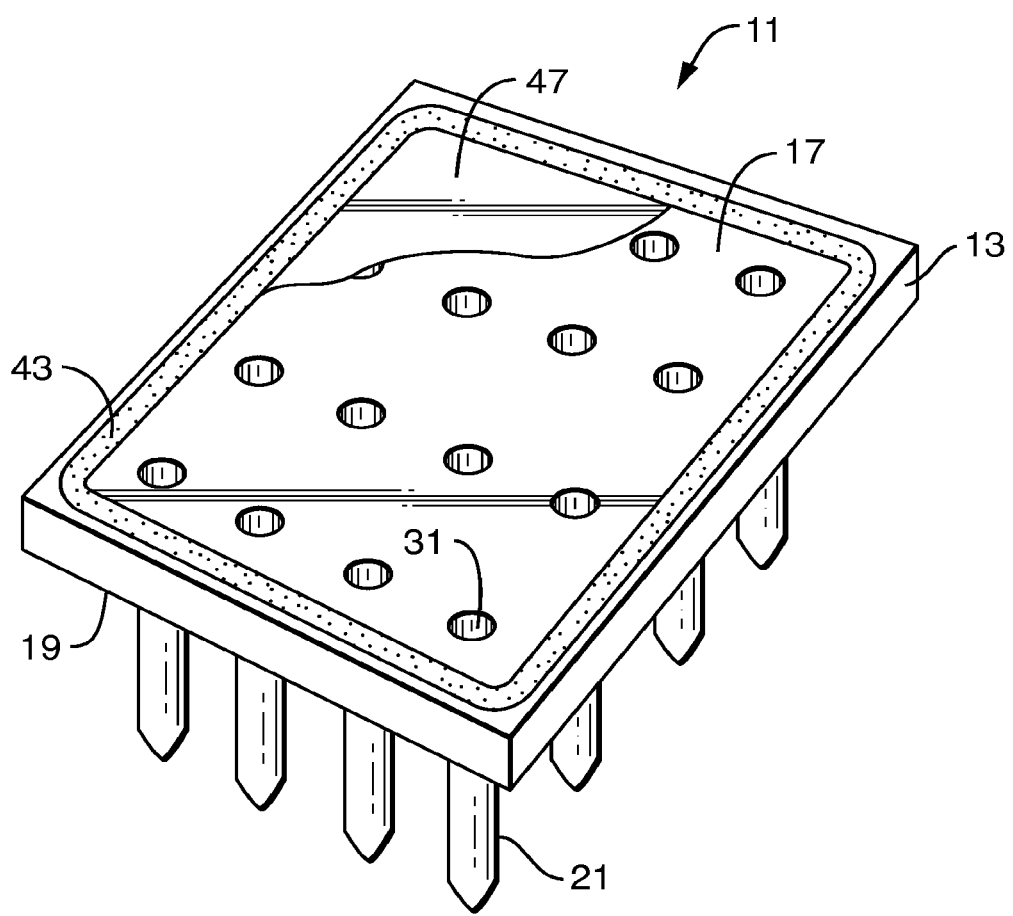
FIG. 1 is a slightly elevated view of a top surface of a device having features of the present invention.
Figure 2:
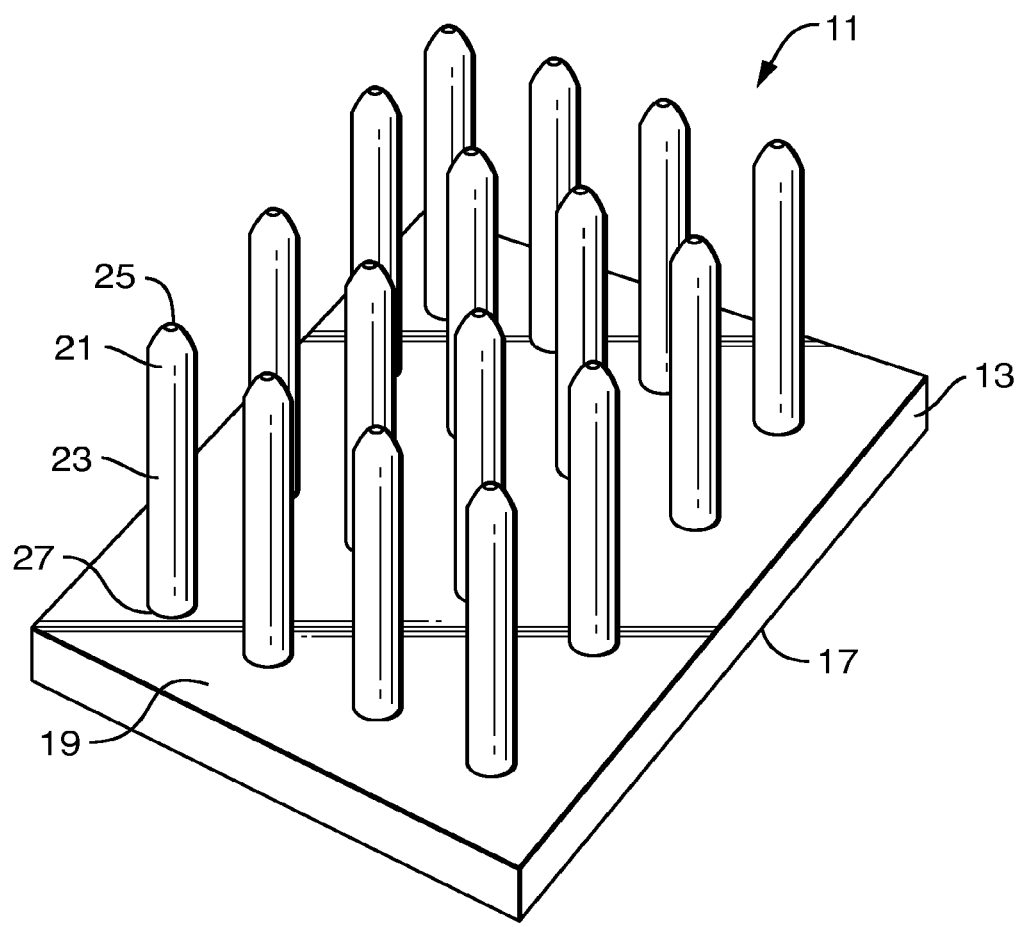
FIG. 2 is a slightly elevated view of the bottom surface of a device having features of the present invention.

Turning now to FIG. 1, a device for sampling blood, generally designated by the numeral 11, is depicted. The device 11 has a platform 13 having a planar configuration, having a top surface 17 and a bottom surface 19, which is best seen in FIG. 2. Platform 13 is made of metals such as stainless steel, aluminum, plastics and the like.

Again, referring to FIG. 2, the bottom surface 19 has one or more microneedles, sixteen are depicted, which for the purpose of clarity only one is designated with the numeral 21. Each microneedle 21 projects from the bottom surface 19 and are arranged in an array. As used herein, the term "array" means a predetermined systematic arrangement of a plurality of microneedles. Although the array depicted is sixteen, smaller numbers of microneedles, as few as three or five, and as many as desired may used. However, to maintain the platform 13 in a size readily handled an upper limit of fifty to one hundred microneedles is preferred. Each side of platform 13 is approximately 0.2 to 0.5 cm.

Techniques for making platforms include those disclosed in Clinical Study: MTS (Microneedle Therapy System), 5-Month Study; Dr. K B Joon, Department of Dermatology, Dongguk University, South Korea (2006); Collagen Induction Therapy Comparison (IPL vs Micro-needling); Drs, H S Moon, S E Kim, D S Ko, A Y Lee, Dep. Of Dermatology, Eulji University School of Medicine and Dongguk University, S. Korea (2006); Product Comparison Study, MTS Roller vs Dermaroller); manufacturer's shelflife and usage study, including known reference on materials and usage. Platforms can be purchased from 3M (Minneapolis, Minn., USA)

Each microneedle 21 has an elongated body 23 having a first end 25 and a second end 27. The first end 25 is formed as a tip and this discussion will use the number designation 25 to refer to both the tip and the first end. The tip 25 is pointed to allow entry into the skin. The second end 27 is formed as a base affixed to the bottom surface 19 of the platform 13. This discussion will use the same number designation to refer to both the base and second end.

The elongated body 23 has a diameter of about 50 to 500 microns and a length of about 200 to 1500 microns. The length of the elongated body conforms with the normal thickness of the total epidermis layer of the skin. The majority of nerve endings are located deeper in the skin such that a microneedle 21, extending its full length into the skin, is unlikely to elicit a response from a nerve. Therefore, the microneedle 21 can be pressed into the skin without eliciting a pain response. The small diameter of each microneedle 21 minimizes the damage to skin layers.

Returning now to FIG. 1, the platform 13 has a passage opening 31 in the top surface 17. Turning now to FIG. 3A, which depicts a single microneedle 21, the passage opening 31 is part of a passage 33 extends to a withdrawal opening 35 in the elongated body 23 at or about the tip 25. The withdrawal opening 35 in the elongated member 23 or at or about the tip 25 is for receiving one or more fluid samples withdrawn as the one or more microneedles are placed on and pressed into the skin of a user.

In the alternative, referring now to FIG. 3B, the passage 33 may be through the platform 13 with the withdrawal opening 35 in the bottom surface 19 in an area is closely associated with one or more microneedle bases 27. The withdrawal opening 35 cooperates with one or more microneedles 21 to receive a fluid sample withdrawn from the skin surface as the microneedle or microneedles 21 are placed on and pressed into the skin of a user.

FIG. 3C depicts a further alternative in which the passage 33 is through the platform 13 with the withdrawal opening 35 in the bottom surface 19 in an area closely associated with one microneedle base 27. The microneedle 21 is formed with a U shaped cross section having a hollow area 37 which functions as an extension of the passage 33 when the microneedle 21 is pressed into the skin of a user. The platform 13 may present a single form of microneedle 21 in an array or a mixture of forms of microneedles 21 of the types represented by FIGS. 3A, 3B and 3C, and modifications of such forms.

Figure 4A:
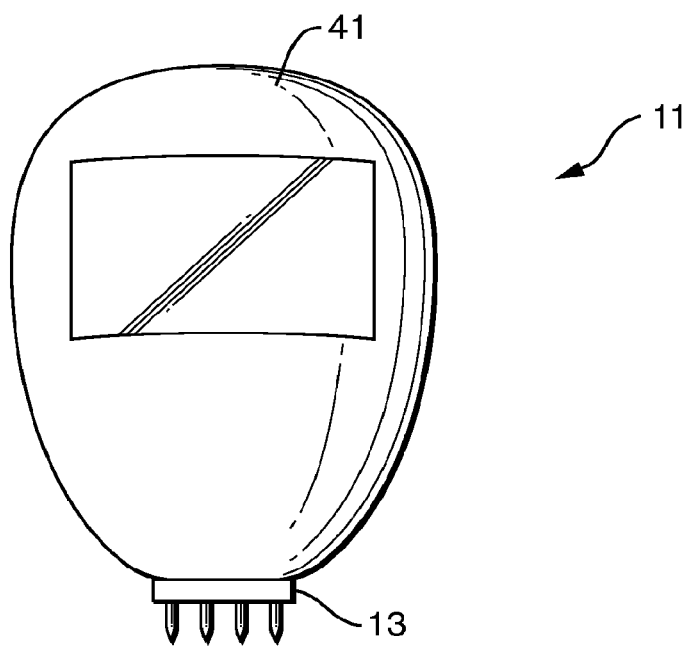
FIGS. 4A and 4B depict a device having a reader.
Figure 4B:
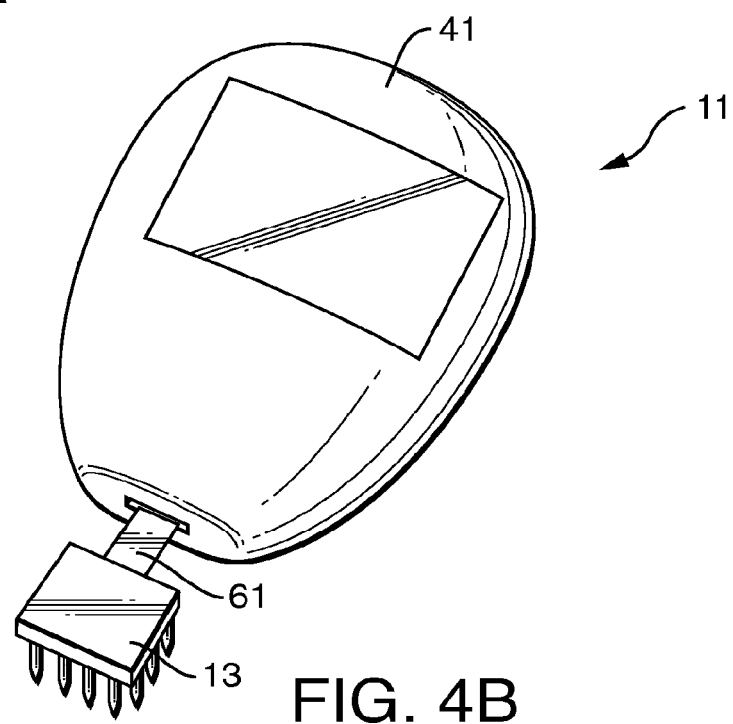

Turning now to FIGS. 4A and 4B, the platform 13 is suited for use with a reader 41. As used herein the term "reader" refers to an instrument that analyses the sample to determine the presence or absence or quantity of one or more compounds of interest. For example, without limitation, for individuals afflicted with diabetes, the compound of interest is glucose. Readers for monitoring glucose levels are well known in the art and are sold under several trademarks such as FreeStyle Freedom®, FreeStyle Flash®, Precision Xtra®, (Abbott Diabetes Care Inc.), Breeze 2®, Contour® (Bayer), OneTouch®Ultra® (Lifescan, Inc), Accu-Chek Aviva®, Accu-Chek Advantage®, Accu-Chek Compact Plus® (Roche), and others. These readers 41 typically have a screen for displaying results but, in the alternative, may also comprise transmission means, for example BLUETOOTH® wireless communication transmitters and receivers, to send results to further receiving equipment [not shown].

FIG. 4A depicts a device 11 having a platform 13 affixed to a reader 41 such that the passage 33 is in fluid communication with the test elements of the reader 41. The platform 13 can be permanently affixed or releaseably affixed to the reader 41. Platforms 13 that are releaseably affixed can be used and replaced with unused platforms 13. Returning now to FIG. 1, platform 13 has an adhesive strip 43 about the outer periphery of top surface 17 to adhere to a reader 41. In another alternative, the adhesive strip 43 coordinates with packaging to facilitate clean aseptic application of the device 11. Other means for affixing platform 13 to a reader 41 comprise mechanical clamping, interfitting or mating platform and reader parts and other means known in the art.

Many readers are intended to work with strips which filter or separate the components of the blood and pass the liquid fraction through one or more developing reagents such as glucose oxidase. Platform 13 receives such strips or filters, such as filter 47 (shown in partial cutaway so as to not obscure other features) in the area about the top surface 17. The filter 47 can be affixed to the platform 13 or placed on the top surface 17 by the user.

Figure 5:
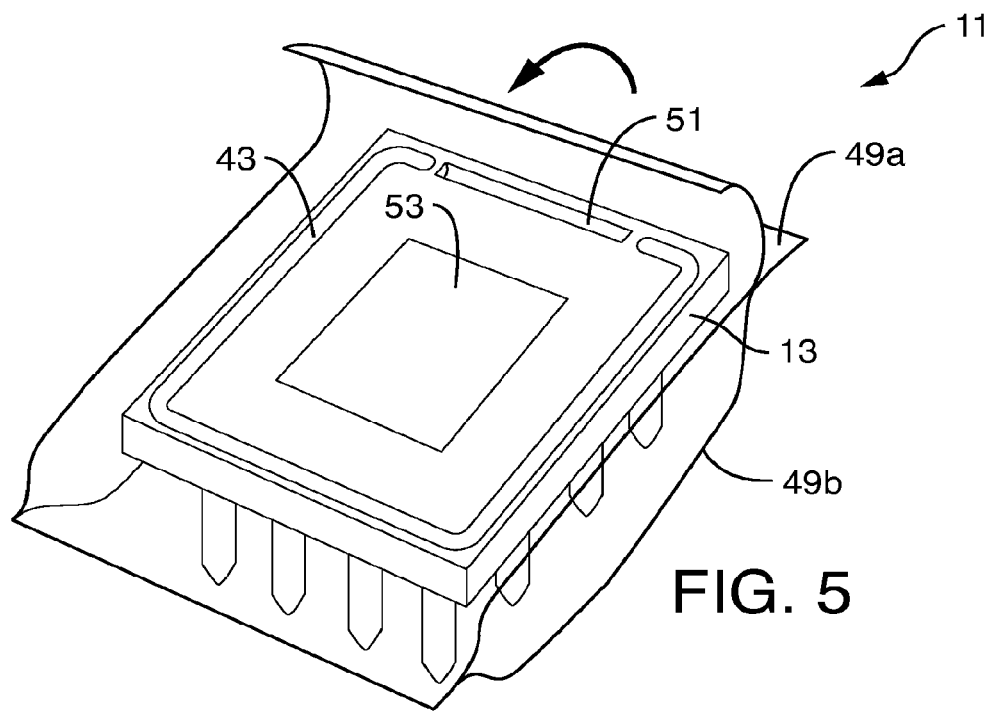
FIG. 5 depicts a device having a reader.

FIG. 4B depicts a device 11 having a reader 41 which receives test strip 61 of a conventional type in association with platform 13. FIG. 5 depicts a platform 13 having an adhesive strip 43 to which a cover sheet 49a is affixed. The device 11 has an open area 51 in which the cover sheet 49a is not secured to allow the open area to receive a test strip [not shown in FIG. 5] of the type known in the art and depicted with the device in FIG. 4B. In the alternative, the test strip is permanently affixed to the platform 13 with or without a cover sheet 49a to form a unitary structure which can be used and disposed of. The cover sheet 49a is used to facilitate handling the platform 13 as it is pressed in the skin.

Figure 6:
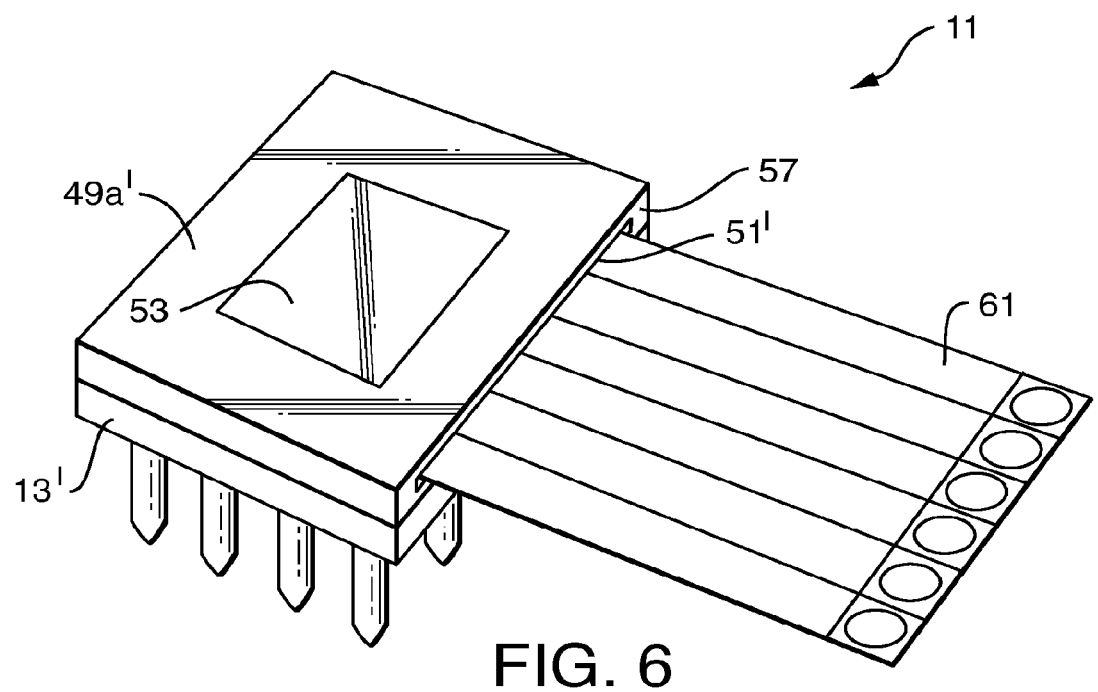
FIG. 6 depicts a device having a capillary strip that connects to a reader.

FIG. 6 depicts a device 11 in which a rigid cover sheet 49a' is affixed to platform 13'. Cover sheet 49a' has a slot 57 creating an open area 51' for receiving a test strip 61 which is permanently affixed to the platform 13'. The device 11 as depicted in FIG. 6 forms a unitary structure which can be used and then disposed of. Cover sheet 49a' has a window 53' or is comprised of a transparent or semi-transparent material to allow the user to see whether blood has been withdrawn and whether test strip 61 is properly in place. FIG. 4B depicts the platform 13' of FIG. 6 with a test strip 61 and a reader 41.

Embodiments of the present invention are ideally suited for monitoring blood glucose levels. Diabetics need to check glucose levels regularly and drawing blood is one of the most unpleasant aspects of the disease.

The operation of the device 11 will now be described in relation to a method of sampling blood. The method comprises the step of providing a platform 13 having a planar configuration with a top surface 17 and a bottom surface 19.

The bottom surface 19 has one or more microneedles 21 projecting therefrom and each microneedle 21 has an elongated body 23 having a first end 25 and a second end 27. The first end 25 is formed as a tip and the second end 27 is formed as a base. The elongated body 23 has a diameter of about 50 to 500 microns and a length of 200 to 1500 microns. The base 27 is affixed to the bottom surface 19 of the platform 13. The platform 13 has a passage opening 31 in the top surface 19 and a passage 33 extending therefrom to a withdrawal opening 35 in at least one of the bottom surface 19, the elongated body 23 and at or about the tip 25.

The method further comprises the step of placing the platform 13 on the skin of a user and pressing the microneedles into the skin to place the withdrawal opening 35 in fluid communication with the user's blood and withdrawing a sample through the passage 33 and out of the passage opening 31.

The blood sample can thus be received directly into a reader 41 or by means of a test strip 61 which can be received by the platform 13 or integrally affixed thereto to form a unitary structure. The microneedles, having a small size in diameter and in length, do not reach nerve ending and do not illicit a pain response.

Thus, the description has presented the best mode contemplated for making and using the present invention with the understanding that the present invention is subject to modification and alteration without departing from the teaching herein. Therefore, the present invention should not be limited to the precise descriptions herein but should encompass the subject matter of the claims that follow and their equivalents.

The invention claimed is:

1. A device for sampling blood from a user, comprising:
   a platform having a planar configuration having a top surface and a bottom surface,
   one or more microneedles projecting from said bottom surface, each microneedle having an elongated body having a first end and a second end, said first end forming a tip and said second end forming a base, said elongated body having a diameter of about 50 to 500 microns and a length of about 200 to 1500 microns, said base affixed to said bottom surface of said platform,
   said platform having a passage opening in said top surface and a passage extending therefrom to a withdrawal opening in at least one of said bottom surface, said elongated body and at or about the tip,
   said withdrawal opening in said bottom surface in an area being closely associated with one or more microneedle bases for cooperating with one or more microneedles to receive a blood sample withdrawn from the skin surface as said one or more microneedles are placed on and pressed into the skin of the user, said withdrawal opening in said elongated member or at or about said tip for receiving one or more blood samples withdrawn as said one or more microneedles are placed on and pressed into the skin of the user, a platform cover forming a conduit in communication with said passage opening for transporting blood or a blood fraction to a reader; and a test strip received on or integrally affixed to said platform in fluid communication with said passage opening for transporting blood or a blood fraction to said reader;

wherein said device is configured for transporting blood or a blood fraction from said one or more blood samples directly from said passage openings to the test strip or the reader.

2. The device of claim 1 wherein said withdrawal opening is in said elongated body or at or about a tip.

3. The device of claim 1 wherein said microneedles have a cross sectional shape of a "U" along their lengths.

4. The device of claim 1 wherein said platform has an array of microneedles.

5. The device of claim 1 wherein said array has between 1 to 50 microneedles.

6. The device of claim 1 wherein said platform cover has window means which allows the user to see that said conduit has a blood sample.

7. The device of claim 1 further comprising a reader.

8. The device of claim 7 wherein said reader detects levels of glucose in the blood or blood fraction.

9. A device for sampling blood from a user, comprising:
a platform having a planar configuration having a top surface and a bottom surface,
one or more microneedles projecting from said bottom surface, each microneedle having an elongated body having a first end and a second end, said first end forming a tip and said second end forming a base, said elongated body having a diameter of about 50 to 500 microns and a length of about 200 to 1500 microns, said base affixed to said bottom surface of said platform,
said platform having a passage opening in said top surface and a passage extending therefrom to a withdrawal opening in at least one of said bottom surface, said elongated body and at or about the tip,
said withdrawal opening in said bottom surface in an area being closely associated with one or more microneedle bases for cooperating with one or more microneedles to receive a blood sample withdrawn from the skin surface as said one or more microneedles are placed on and pressed into the skin of the user, said withdrawal opening in said elongated member or at or about said tip for receiving one or more blood samples withdrawn as said one or more microneedles are placed on and pressed into the skin of the user,
wherein said platform is received directly on a reader; and
wherein said device is configured for transporting blood or a blood fraction from said one or more blood samples directly from said passage openings to a test strip or the reader.

10. The device of claim 9 wherein said reader detects levels of glucose in the blood or blood fraction.

11. A method of sampling blood from a user, comprising the steps of:
providing a platform having a planar configuration having a top surface and a bottom surface, said bottom surface having one or more microneedles projecting therefrom and each microneedle having an elongated body having a first end and a second end, said first end forming a tip and said second end forming a base, said elongated body having a diameter of about 50 to 500 microns and a length of about 200 to 1500 microns, said base affixed to said bottom surface of said platform, said platform having a passage opening in said top surface and a passage extending therefrom to a withdrawal opening in at least one of said bottom surface, said elongated body and at or about the tip, said withdrawal opening in said bottom surface in an area closely associated with one or more microneedle bases for cooperating with one or more microneedles to receive a blood sample withdrawn from the skin surface as said one or more microneedles are placed on and pressed into the skin of the user, said withdrawal opening in said elongated member or at or about said tip for receiving one or more blood samples withdrawn as said one or more microneedles are placed on and pressed into the skin of the user, a test strip received on or integrally affixed to said platform and in fluid communication with said passage opening for transporting blood or a blood fraction to said reader, wherein said device is configured for transporting blood or a blood fraction from said one or more blood samples directly from said passage openings to the test strip or the reader; and
placing said platform on the skin of the user and pressing said microneedles into said skin to place said withdrawal opening in fluid communication with the users blood; and
withdrawing a blood sample through said passage and out of said passage opening.

12. The method of claim 11 wherein said platform has an array of microneedles.

13. The method of claim 12 wherein said array has between 1 and 50 microneedles.

14. The method of claim 11 further comprising a platform cover forming a conduit in communication with said passage opening for transporting blood or a blood fraction to a reader.

15. The method of claim 14 wherein said platform cover has window means which allows the user to see that said conduit has a blood sample and said method comprises the step of checking the window for the presence of a sample.

16. The method of claim 11 wherein said sample is received by a reader.

17. The method of claim 16 wherein said reader detects s of glucose in the blood or blood fraction.

* * * * *